United States Patent [19]

Morozowich

[11] 4,136,115

[45] Jan. 23, 1979

[54] INTER-PHENYLENE-PG CARBONYL- OR CYANO-SUBSTITUTED AMIDES

[75] Inventor: Walter Morozowich, Kalamazoo Township, Kalamazoo County, Mich.

[73] Assignee: The Upjohn Company, Kalamazoo, Mich.

[21] Appl. No.: 898,253

[22] Filed: Apr. 20, 1978

Related U.S. Application Data

[63] Continuation-in-part of Ser. No. 788,455, Apr. 18, 1977, Pat. No. 4,100,192.

[51] Int. Cl.$^2$ .............................................. C07C 177/00
[52] U.S. Cl. ........................... 260/559 R; 260/559 B; 260/465 F; 560/45
[58] Field of Search ................. 260/559 R, 559 B, 45, 260/465 F

[56] References Cited

U.S. PATENT DOCUMENTS 4,054,604  10/1977  Bernady et al. ................. 260/559 R

OTHER PUBLICATIONS

Derwent Abstract, 09166X/05 US 3933895, 09167X/05 US 3933896, 09168X/05 US 3933897, 09169X/05 US 3933898, 20-01-76.

*Primary Examiner*—Paul J. Killos
*Attorney, Agent, or Firm*—Robert A. Armitage

[57] ABSTRACT

The present invention relates to inter-phenylene PG carbonyl- or cyano-substituted amides. These compounds are pharmacological agents, being prolonged orally active platelet aggregation inhibitors in mammalian species. These compounds are accordingly useful for antithrombotic applications.

50 Claims, No Drawings

INTER-PHENYLENE-PG CARBONYL- OR CYANO-SUBSTITUTED AMIDES

CROSS REFERENCE TO RELATED APPLICATIONS

This application is a continuation-in-part of Ser. No. 788,455, filed Apr. 18, 1977, now U.S. Pat. No. 4,100,192, issued July 11, 1978.

The present invention relates to inter-phenylene-PG carbonyl- or cyano-substituted amides, the essential material constituting a disclosure of which is incorporated here by reference from Ser. No. 788,455. In particular, the present invention relates to inter-phenylene-PG carbonyl- or cyano-substituted amides of the unsubstituted inter-phenylene PG amides described in Ser. No. 788,455 now U.S. Pat. 4,100,192.

I claim:

1. A prostaglandin analog of the formula

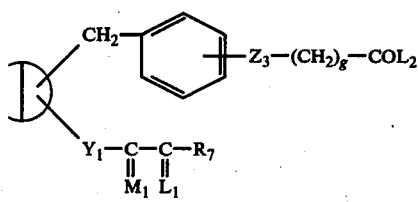

wherein D is

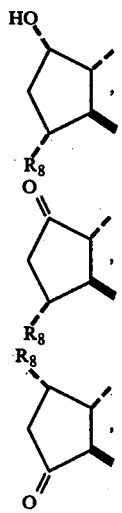

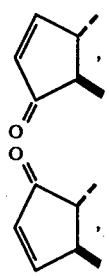

wherein $R_8$ is hydrogen or hydroxy;
wherein $Y_1$ is
(1) trans-CH=CH—,
(2) cis—CH=CH—, or
(3) —CH$_2$CH$_2$—, wherein g is one, 2, or 3;
wherein $Z_3$ is oxa or methylene, with the proviso that $Z_3$ is oxa only when $R_3$ and $R_4$ are hydrogen or methyl, being the same or different;
wherein $L_1$ is

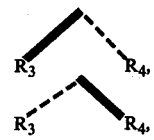

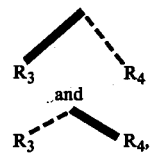

or a mixture of

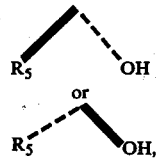

wherein $R_3$ and $R_4$ are hydrogen, methyl, or fluoro, being the same or different, with the proviso that one of $R_3$ and $R_4$ is methyl only when the other is hydrogen or methyl;
wherein $M_1$ is

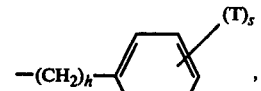

or

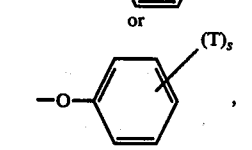

wherein $R_5$ is hydrogen or methyl; wherein $R_7$ is
(1) —(CH$_2$)$_m$—CH$_3$, $$-(CH_2)_h- \text{(phenyl)}(T)_s \quad (2)$$

or $$-O-\text{(phenyl)}(T)_s \quad (3)$$

wherein h is zero to 3, inclusive, wherein m is one to 5, inclusive, s is zero, one, 2, or 3, and T is chloro, fluoro, trifluoromethyl, alkyl of one to 3 carbon atoms, or alkoxy of one to 3 carbon atoms, the various T's being the same or different, with the proviso that not more than two T's are other than alkyl; and
wherein $L_2$ is
amino of the formula —NR$_{21}$R$_{22}$, wherein one $R_{21}$ and $R_{22}$ is hydrogen or alkyl of one to 12 carbon atoms, inclusive; and the other of $R_{21}$ and $R_{22}$ is
(i) phenyl substituted with zero, one, or 2 nitro, chloro, alkyl of one to 3 carbon atoms, inclusive, or hydroxy and at least one but not more than three carboxy or alkoxycarbonyl of one to 4 carbon atoms, inclusive, with the overall proviso that there be not more than 3 substituents;
(ii) carboxyalkyl of one to 4 carbon atoms, inclusive;
(iii) carbamoylalkyl of one to four carbon atoms, inclusive,
(iv) cyanoalkyl of one to 4 carbon atoms, inclusive;

(v) acetylalkyl of one to 4 carbon atoms, inclusive;
(vi) benzoylalkyl of one to 4 carbon atoms, inclusive, or
(vii) benzoylalkyl substituted by one, 2, or 3 chloro, alkyl of one to 3 carbon atoms inclusive, hydroxy, alkoxy of one to 3 carbon atoms, inclusive, carboxy, alkoxycarbonyl of one to 4 carbon atoms, inclusive, or nitro.

2. A prostaglandin analog according to claim 1, wherein D is

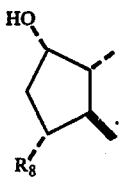

3. A prostaglandin analog according to claim 2, wherein $R_8$ is hydrogen.

4. 3,7-inter-m-Phenylene-3-oxa-4,5,6-trinor-11-deoxy-PGF$_1\alpha$, p-carboxyanilide, a prostaglandin analog according to claim 3.

5. A prostaglandin analog according to claim 2, wherein $R_8$ is hydroxy.

6. 3,7-inter-m-Phenylene-3-oxa-4,5,6-trinor-PGF$_1\alpha$, p-carboxyanilide, a prostaglandin analog according to claim 5.

7. A prostaglandin analog according to claim 1, wherein D is

8. A prostaglandin analog according to claim 7, wherein $R_8$ is hydrogen.

9. 3,7-inter-m-Phenylene-3-oxa-4,5,6-trinor-9-deoxy-PGD$_1$, p-carboxyanilide, a prostaglandin analog according to claim 8.

10. A prostaglandin analog according to claim 7, wherein $R_8$ is hydroxy.

11. 3,7-inter-m-Phenylene-3-oxa-4,5,6-trinor-PGD$_1$, p-carboxyanilide, a prostaglandin analog according to claim 10.

12. A prostaglandin analog according to claim 1, wherein D is

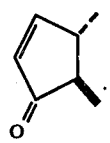

13. 3,7-inter-m-Phenylene-3-oxa-4,5,6-trinor-9-deoxy-9,10-didehydro-PGD$_1$, p-carboxyanilide, a prostaglandin analog according to claim 12.

14. A prostaglandin analog according to claim 1, wherein D is

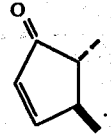

15. 3,7-inter-m-Phenylene-3-oxa-4,5,6-trinor-PGA$_1$, p-carboxyanilide, a prostaglandin analog according to claim 14.

16. A prostaglandin analog according to claim 1, wherein D is

17. A prostaglandin analog according to claim 16, wherein $R_8$ is hydrogen.

18. 3,7-inter-m-Phenylene-3-oxa-4,5,6-trinor-13,14-dihydro-11-deoxy-PGE$_1$, p-carboxyanilide, a prostaglandin analog according to claim 17.

19. A prostaglandin analog according to claim 16, wherein $R_8$ is hydroxy.

20. A prostaglandin analog according to claim 19, wherein $Y_1$ is cis—CH=CH—.

21. 3,7-inter-m-Phenylene-3-oxa-4,5,6-trinor-cis-13-PGE$_1$, p-carboxyanilide, a prostaglandin analog according to claim 20.

22. A prostaglandin analog according to claim 19, wherein $Y_1$ is CH$_2$CH$_2$—.

23. 3,7-inter-m-Phenylene-3-oxa-4,5,6-trinor-13,14-dihydro-PGE$_1$, p-carboxyanilide, a prostaglandin analog according to claim 22.

24. A prostaglandin analog according to claim 19, wherein $Y_1$ is trans—CH=CH—.

25. A prostaglandin analog according to claim 24, wherein $Z_3$ is methylene.

26. A prostaglandin analog according to claim 25, wherein $Z_3$ is attached to the phenyl ring in the position meta to methylene.

27. 3,7-inter-m-Phenylene-4,5,6-trinor-PGE$_1$, p-carboxyanilide, a prostaglandin analog according to claim 26.

28. A prostaglandin analog according to claim 24, wherein $Z_3$ is oxa.

29. A prostaglandin analog according to claim 28, wherein $M_1$ is

30. 15-epi-3,7-inter-m-Phenylene-3-oxa-4,5,6-trinor-PGE$_1$, p-carboxyanilide, a prostaglandin analog according to claim 29.

31. A prostaglandin analog according to claim 28, wherein $M_1$ is

32. A prostaglandin analog according to claim 31, wherein $Z_3$ is attached to the phenyl ring in the position meta to methylene.

33. A prostaglandin analog according to claim 32, wherein $R_7$ is

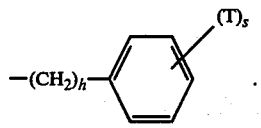

34. 3,7-inter-m-Phenylene-3-oxa-17-phenyl-4,5,6,18,19,20-hexanor-PGE$_1$, p-carboxyanilide, a prostaglandin analog according to claim 33.

35. A prostaglandin analog according to claim 32, wherein $R_7$ is

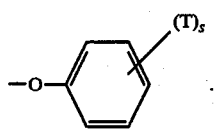

36. 3,7-inter-m-Phenylene-3-oxa-16-phenoxy-4,5,6,17,18,-19,20-heptanor-PGE$_1$, p-carboxyanilide, a prostaglandin analog according to claim 35.

37. A prostaglandin analog according to claim 32, wherein $R_7$ is $-(CH_2)_m-CH_3$.

38. A prostaglandin analog according to claim 37, wherein m is 3.

39. A prostaglandin analog according to claim 38, wherein g is 3.

40. 2a,2b-Dihomo-3,7-inter-m-phenylene-3-oxa-4,5,6-trinor-PGE$_1$, p-carboxyanilide, a prostaglandin analog according to claim 39.

41. A prostaglandin analog according to claim 38, wherein g is 1.

42. A prostaglandin analog according to claim 41, wherein at least one of $R_3$ and $R_4$ is methyl.

43. 3,7-inter-m-Phenylene-3-oxa-4,5,6,-trinor-16,16-dimethyl-PGE$_1$, p-carboxyanilide, a prostaglandin analog according to claim 42.

44. A prostaglandin analog according to claim 41, wherein at least one of $R_3$ and $R_4$ is fluoro.

45. 3,7-inter-m-Phenylene-3-oxa-4,5,6-trinor-16,16-difluoro-PGE$_1$, p-carboxyanilide, a prostaglandin analog according to claim 44.

46. A prostaglandin analog according to claim 41, wherein $R_3$ and $R_4$ are both hydrogen.

47. A prostaglandin analog according to claim 46, wherein $R_5$ is methyl.

48. 3,7-inter-m-Phenylene-3-oxa-4,5,6-trinor-15-methyl- PGE$_1$, p-carboxyanilide, a prostaglandin analog according to claim 47.

49. A prostaglandin analog according to claim 46, wherein $R_5$ is hydrogen.

50. 3,7-inter-m-Phenylene-3-oxa-4,5,6-trinor-PGE$_1$, P-carboxyanilide, a prostaglandin analog according to claim 49.

* * * * *

UNITED STATES PATENT AND TRADEMARK OFFICE
CERTIFICATE OF CORRECTION

PATENT NO. : 4,136,115
DATED : January 23, 1979
INVENTOR(S) : W. Morozowich

It is certified that error appears in the above—identified patent and that said Letters Patent are hereby corrected as shown below:

Column 2, line 55, "one $R_{21}$" should read -- one of $R_{21}$ --;

Column 4, line 36, "$CH_2CH_2$-" should read -- -$CH_2CH_2$- --;

Column 6, line 30, "P-carboxyanilide," should read -- p-carboxyanilide--

Signed and Sealed this

Twenty-fourth Day of July 1979

[SEAL]

Attest:

LUTRELLE F. PARKER
*Attesting Officer*     *Acting Commissioner of Patents and Trademarks*